United States Patent
Cox et al.

(10) Patent No.: US 12,246,081 B2
(45) Date of Patent: Mar. 11, 2025

(54) DEODORANT COMPOSITIONS

(71) Applicant: Conopco, Inc., Englewood Cliffs, NJ (US)

(72) Inventors: Diana Sheila Cox, Bedford (GB); Alexander Gordon James, Higham Ferrers (GB); Mrinalini Jayant Puranik, Karnataka (IN); David William Thornthwaite, Little Neston (GB); Jason Richard Williams, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 524 days.

(21) Appl. No.: 16/769,518

(22) PCT Filed: Dec. 12, 2018

(86) PCT No.: PCT/EP2018/084639
§ 371 (c)(1),
(2) Date: Jun. 3, 2020

(87) PCT Pub. No.: WO2019/121269
PCT Pub. Date: Jun. 27, 2019

(65) Prior Publication Data
US 2020/0383891 A1    Dec. 10, 2020

(30) Foreign Application Priority Data
Dec. 20, 2017  (EP) ..................... 17209154

(51) Int. Cl.
*A61K 8/49*    (2006.01)
*A61K 8/66*    (2006.01)
*A61Q 15/00*   (2006.01)

(52) U.S. Cl.
CPC ............ *A61K 8/49* (2013.01); *A61K 8/66* (2013.01); *A61Q 15/00* (2013.01); *A61K 2800/59* (2013.01); *A61K 2800/78* (2013.01)

(58) Field of Classification Search
CPC .......... A61K 8/49; A61K 8/66; A61Q 15/00
See application file for complete search history.

(56) References Cited

U.S. PATENT DOCUMENTS

| 3,243,346 | A | * | 3/1966 | Bechmann | A61K 8/49 548/201 |
| 5,047,409 | A | * | 9/1991 | Di Schiena | A61K 8/49 424/47 |
| 6,251,927 | B1 | * | 6/2001 | Lai | A61K 31/426 514/371 |
| 7,018,978 | B2 | * | 3/2006 | Miracle | A61K 8/49 568/591 |
| 7,442,369 | B1 | * | 10/2008 | Pena | A61K 8/4953 424/78.02 |
| 2008/0219942 | A1 | * | 9/2008 | Chambers | A61K 8/982 424/70.2 |

FOREIGN PATENT DOCUMENTS

| CN | 104069525 A | * | 10/2014 |
| FR | 2773323 | | 9/1999 |
| WO | WO0239976 | | 5/2002 |
| WO | WO2006079934 | | 8/2006 |
| WO | WO2009111988 | | 9/2009 |
| WO | WO2010031657 | | 3/2010 |

OTHER PUBLICATIONS

Williams et al., "Chapter 2. Drug Design and Relationship of Functional Groups to Pharmacologic Activity," Foye's Principles of Medicinal Chemistry, Fifth Edition, Copyright 2002, pp. 37-67.*
Starkenmann et al., Identification of the Precursor of (s)-3-Methyl-3-sulfanylhexan-1-ol, the Sulfury Malodour of Human Axilla Sweat, Chemistry and Biodiversity, 2005, 2, pp. 705-716.
Chen et al., Determination of thiols and disulfides via HPLC quantification of 5-thio-2-nitrobenzoic acid, J Pharm Biomed Anal., Dec. 15, 2008; 48(5): 1375-1380.
Bawdon et al.; Identification of axillary *Staphylococcus* sp. involved in the production of the malodorous thioalcohol 3-methyl-3-sufanylhexan-1-ol; FEMS Microbiology Letters; 2015; pp. 1-10; XP055342282; vol. 362, No. 16.
IPRP1 in PCTEP20180846399; Jun. 23, 2020.
Egert et al.; Identification of compounds inhibiting the C—S lyase activity of a cell extract from a *Staphylococcus* sp. isolated from human skin; Letters in Applied Microbiology; 2013; pp. 534-539; vol. 57, No. 6.
Search Report and Written Opinion in EP17209154; Mar. 9, 2018.
Search Report and Written Opinion in PCTEP2018084639.

* cited by examiner

*Primary Examiner* — Alton N Pryor
(74) *Attorney, Agent, or Firm* — GREENBERG TRAURIG, LLP

(57) ABSTRACT

The present invention relates to a deodorant composition comprising an oxazolidine- or, a thiazolidine-carboxylic acid compound, a cosmetic carrier and optionally a fragrance. The invention also relates to a manufacturing process for the deodorant composition, a method of treating malodour and a method of screening deodorant actives as well as inhibiting a *Staphylococcus hominis* C-S ≥-lyase.

9 Claims, No Drawings

DEODORANT COMPOSITIONS

RELATED APPLICATIONS

This application is a national phase filing under 35 USC 371 of International Application No. PCT/EP2018/084639, filed on Dec. 12, 2018, which claims priority from European Patent Application No. 17209154.8, filed Dec. 20, 2017, the contents of which are incorporated herein in their entirety for all purposes.

FIELD OF THE INVENTION

The present invention relates to the field of deodorant compositions and methods of supressing human body odour.

BACKGROUND TO THE INVENTION

It is generally accepted that the microbial community of the human axilla plays a key role in the formation of body odour. In several cases, the non-volatile malodour precursors are excreted onto the skin, from which the volatile odorous parts are subsequently released by microbial enzyme activities. It is known that the smell of the thioalcohol 3-methyl-3-sulfanylhexan-1-ol (3M3SH) released from its precursor S-(1-(2-hydroxyethyl)-1-methylbutyl)-(L)-cysteinylglycine (Cys-Gly-3M3SH) or Cys-3M3SH is particularly intense. 3M3SH is perceptible by the human nose at concentrations as low as 1-3 pg $L^{-1}$ (Natsch et al, Chem Biodivers 2004; 1, 1058-72). Historically, C-S β-lyase enzymes (e.g. cystathionine-β-lyase) have been hypothesized to be involved in the final catabolic step of Cys-Gly-3M3SH biotransformation, namely the conversion of S-[1-(2-hydroxyethyl)-1-methylbutyl]-(L)-cysteine (Cys-3M3SH) to 3M3SH.

WO10/031657A2 describes the use of urea derivatives and phenacylthiazolium salts for inhibition of C-S-β-lyase, and for the prevention or treatment of body odour.

WO06/079934A2 describes a screening method for compounds having the ability to prevent, treat or reduce malodour on body surfaces which includes adding the malodour precursor to a medium comprising the compound to be screened and at least one functional β-lyase enzyme or a bacterial strain selected from the family of *Staphylococcus*.

FEMS Microbiol. Lett., 263(16), 2015, fnv111 identifies the bacterial species *Staphylococcus hominis, Staphylococcus haemolyticus* and *Staphylococcus lugdunensis* as being particularly efficient Cys-Gly-3M3SH transformers.

Letts in Applied Microbiol., 57(6), 2013 identifies compounds inhibiting the C-S □-lyase activity of a cell extract from a *Staphylococcus* species. isolated from human skin.

WO 91/11988 describes a method of suppressing body odour by utilizing a compound which is capable of serving as an alternative substrate to the naturally occurring malodour-producing precursor, in an amount effective to reduce the conversion of malodour-producing precursor. The malodour is thought to be generated by *Staphylococcus* and several *Corynebacterium* isolates in the presence of apocrine secretion.

Despite all the prior art and a variety of bacterial strains having been isolated from axillary skin, it is still subject to debate as to which bacterial species is the most effective for transforming malodour precursor. Furthermore, it remains a desire to identify new and/or improved deodorant actives, deodorant compositions and methods of treating malodour on the surface of the human body.

SUMMARY OF THE INVENTION

In a first aspect of the present invention, there is provided a deodorant composition comprising: (1) an oxazolidine-carboxylic acid compound or a thiazolidine-carboxylic acid compound as further defined below and (2) a cosmetic carrier.

In a second aspect of the present invention, there is provided a method of treating malodour comprising topical application of the oxazolidine- or, thiazolidine-carboxylic acid compound as described in the first aspect of the invention, particularly from a deodorant composition.

In a third aspect of the present invention, there is provided a manufacturing process for a deodorant composition according to the first aspect, comprising a step of dissolving or homogeneously dispersing the oxazolidine- or, thiazolidine-carboxylic acid compound as described in the first aspect in a cosmetic carrier.

In a fourth aspect of the present invention, there is provided a method of screening deodorant actives, comprising the steps of providing a medium containing a malodour precursor and *S. hominis* C-S β-lyase, adding to the medium an oxazolidine- or, thiazolidine-carboxylic acid compound as described in the first aspect of the invention as the compound to be screened and measuring the release of 3M3SH in comparison with a control cell lacking the compound to be screened.

In the above indicated fourth aspect of the invention, the malodour precursor is preferably Cys-3M3SH.

In a fifth aspect of the present invention, there is provided a method of inhibiting *S. hominis* C-S β-lyase, comprising a step of mixing the said enzyme with an oxazolidine- or, thiazolidine-carboxylic acid compound as described in the first aspect of the invention.

Herein, "inhibiting" should be understood to mean reducing the effectiveness of said enzyme in its conversion of thiol malodour precursors to thiol malodours.

An objective of the present invention is to provide an improved deodorant composition. An associated objective is to provide a manufacturing process for the said composition.

Another objective of the present invention is to provide a method of treating malodour on the surface of human body without affecting the number of microbes thereon. The said method does not involve the use of anti-microbial compounds, in particular broad-spectrum anti-microbials.

Herein, an "anti-microbial" should be understood to mean a material that reduces the number of microbes, in particular the number of bacteria, following its administration.

A further objective of the present invention is to provide a screening method for new deodorant actives.

Herein, an oxazolidine-carboxylic acid compound should be understood to be a compound comprising an oxazolidine-carboxylic acid group and a thiazolidine-carboxylic acid compound should be understood to be a compound comprising a thiazolidine-carboxylic acid group.

Surprisingly, it has been found that a compound comprising an oxazolidine-carboxylic acid group or a thiazolidine-carboxylic acid group, as further defined hereinbelow, can affect a C-S β-lyase enzyme present in bacterial species particularly responsible for malodour development on the surface of the human body. Further, a cosmetic composition comprising said compound is capable of treating malodour on the surface of human body.

DETAILED DESCRIPTION OF THE INVENTION

Herein, any feature of a particular embodiment of the present invention may be utilized in any other embodiment of the invention.

Any feature described as 'preferred' should be understood to be particularly preferred in combination with a further preferred feature or features.

Herein, any feature stated as preferred in a particular aspect of the invention should be understood to be a preferred feature in the other aspects of the invention.

The word 'comprising' is intended to mean 'including' but not necessarily 'consisting of' or 'composed of'. The examples given in the description below are intended to clarify the invention but not to limit the invention. All weight percentages (wt %) are based upon the final weight of the composition unless indicated otherwise. Numerical ranges expressed in the format 'x-y' are understood to include x and y, unless specified otherwise. The numbers can be qualified by the term 'about'. When for a specific feature multiple preferred ranges are described in the format 'from x to y', it is understood that all ranges combining the different endpoints are also contemplated.

'Cosmetic use' should be understood to mean non-therapeutic use and 'cosmetic composition' to mean composition suitable for cosmetic use.

'In use' or 'during use', should be understood to mean throughout the course or duration of treating body malodour, which may include the steps of, but not limited to, applying the treatment to the desired area, leaving the treatment thereon, subsequently rinsing off the treatment and re-applying.

'Cosmetic carrier' should be understood to mean a carrier that is compatible with the skin and/or its integuments or mucous membranes, not causing any unacceptable discomfort liable to discourage the consumer from using and preferably, having pleasant colour, odour and/or feel.

'Treating malodour or body odour' should be understood to mean control, suppress, reduce, or prevent the formation of unpleasant odours on the surface of the human body. 'Deodorant active' is a compound that by itself is capable of treating the body odour.

The present invention involves effects upon an odour-generating C-S β-lyase, in particular such enzymes present in *S. hominis*, *S. haemolyticus* and *S. lugdunensis*. The enzyme may be cloned from *S. hominis* strain B10, which has been demonstrated to be responsible for the conversion of S-cysteine-conjugated precursor (Cys-3M3SH) to the malodour compound 3M3SH. *S. hominis* C-S β-lyase is found much less susceptible to inhibition by classical inhibitors such as aminoethoxyvinyl glycine, aminooxyacetic acid and L-cycloserine. The reason for the ineffectiveness of classical inhibitor is unclear.

Surprisingly, we have found that a compound comprising a thiazolidine carboxylic acid group or an oxazolidine carboxylic acid group as further defined hereinbelow, can inhibit *S. hominis* C-S β-lyase and is capable of serving as a deodorant active.

The thiazolidine carboxylic acid or oxazolidine carboxylic acid compound has the formula (I) below:

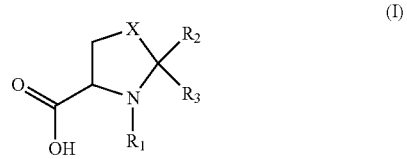

(I)

wherein X is S or O; $R_1$, $R_2$ and $R_3$ can be the same or different, individually selected from hydrogen, C1-C20 linear, branched, or cyclic alkyl, alkenyl, or aryl residue, or mixtures thereof and $R_2$ and $R_3$ can be linked to form a cyclic structure. $R_1$, $R_2$ and $R_3$ are each optionally substituted and optionally comprising one or more heteroatoms.

In addition, or alternatively, the composition may comprise an oxazolidine- or thiazolidine-carboxylic acid compound that is an ester or salt of a compound of formula (I) or is a compound that releases a compound of formula (I) in use.

In preferred embodiments, the composition of the invention comprises thiazolidine carboxylic acid or oxazolidine carboxylic acid of formula I.

In certain preferred embodiments, X is S (a sulphur atom), making the compound a thiazolidine carboxylic acid.

Preferably, $R_1$, $R_2$ and $R_3$, if substituted, are substituted by one or more hydroxyl, carbonyl, carboxyl, phenyl, ester, alkoxy or mixtures thereof, optionally comprising one or more heteroatoms preferably selected from N, O, F, Cl, Br, I.

Preferably, $R_1$ is selected from hydrogen, carbonyl, carboxyl, phenyl, ester, alkoxy or mixtures thereof while $R_2$ and $R_3$ are selected from hydrogen, C1-C20 linear, branched, or cyclic alkyl, alkenyl, or aryl residue, or mixtures thereof, optionally substituted by one or more groups preferably selecting from hydroxyl, carbonyl, carboxyl, phenyl, ester alkoxy, or mixtures thereof and optionally comprising one or more heteroatoms preferably selected from N, O, F, Cl, Br, I. More preferably, $R_1$ is selected from hydrogen, carbonyl, carboxyl, phenyl, ester or mixtures thereof. Still more preferably, $R_1$ is selected from hydrogen, carbonyl, carboxyl, phenyl, ester or carboxybenzyl (Cbz). Most preferably, $R_1$ is hydrogen. In certain preferred embodiments, when X is O (an oxygen atom), $R_1$ is carboxybenzyl (Cbz) or hydrogen, preferably Cbz; when X is S (a sulphur atom), $R_1$ is hydrogen.

Preferably, $R_2$ and $R_3$ are individually selected from hydrogen, C1-C20 linear, branched, or cyclic alkyl, alkenyl, or aryl residue, or mixtures thereof; $R_2$ and $R_3$ can be linked to form a cyclic structure; $R_2$ and $R_3$ are each optionally substituted by one or more hydroxyl, carbonyl, carboxyl, phenyl, ester, alkoxy or mixtures thereof and optionally comprising one or more heteroatoms selected from N, O, F, Cl, Br, I. For example, R2 and R3 can be individually selected from H, C1-6 linear, branched, cyclic alkyl or alkenyl. In a preferred embodiment, the substitution comprises one or more hydroxyl, alkoxy, saturated or unsaturated rings, or mixtures thereof, optionally comprising one or more O, N or halides. For example, the substitution is a phenyl or a cyclohexyl. In another preferred embodiment, the substitution comprises one or more 5 or 6-membered rings optionally comprising one or more O, N, Cl and Br. For example, the substitution is a phenol or p-bromo-phenol. In yet another preferred embodiment, $R_2$ is selected from hydrogen, C1-C20 linear, branched, or cyclic alkyl, alkenyl, or aryl residue, or mixtures thereof, substituted by a group comprising one or more 5 or 6-membered rings optionally comprising one or more O, N, Cl and Br and $R_3$ is a hydrogen or C1-C20 linear, branched, or cyclic alkyl, alkenyl, or aryl residue, or mixtures thereof, preferably a hydrogen or C1-C20 linear, branched alkyl or alkenyl, more preferably a hydrogen or C1-C20 linear, branched alkyl. For example, if $R_2$ and $R_3$ are linked to form a cyclic structure, the structure can be a cyclohexyl, a tetrahydropyran, piperidine, or a piperidine substituted by a phenyl. For another example, $R_3$ is hydrogen or alkyl and $R_2$ can be hydrogen, alkyl, (substituted) benzyl, furan, or an alkyl substituted by phenol.

Any of the preference of X, $R_1$, $R_2$ and $R_3$ may be utilized in combination with any other preference of X, $R_1$, $R_2$ and $R_3$.

According to preferred embodiments, the compound can be selected from 2-(3-hydroxy-4-methoxy-phenyl)-thiazolidine-4-carboxylic acid, 2-(4-hydroxy-3-methoxyphenyl)-1,3-thiazolidine-4-carboxylic acid, 1,4-dioxa-9-thia-12-azadispiro [4.2.4.2] tetradecane-11-carboxylic acid, 2-(2-furyl)-1,3-thiazolidine-4-carboxylic acid, 2-(1-ethylpropyl)-4-thiazolidinecarboxylic acid, 1-thia-4-azaspiro[4.5]decane-3-carboxylic acid, 8-benzyl-1-thia-4,8-diazaspiro[4.5]decane-3-carboxylic acid, 2-phenylthiazolidine-4-carboxylic acid, 2-[4-(allyloxy)phenyl]-1,3-thiazolidine-4-carboxylic acid, 2-(4-methoxyphenyl)-1,3-thiazolidine-4-carboxylic acid, 2-hexyl-1,3-thiazolane-4-carboxylic acid, 2-(2-hydroxy-phenyl)-thiazolidine-4-carboxylic acid, 2-benzyl-1,3-thiazolidine-4-carboxylic acid, 2,2-dimethyl-4-thiazolidine-4-carboxylic acid, 2-ethyl-thiazolidine-4-carboxylic acid, 2-benzo(1,3)dixol-5-yl-thiazolidine-4-carboxylic acid, 2-(2-chloro-phenyl)-thiazolidine-4-carboxylic acid, 3-acetyl-2-phenyl-4-thiazolidinecarboxylic acid, 2-(5-bromo-2-hydroxyphenyl)thiazolidine-4-carobxylic acid, (S)-(–)-3-(benzyloxycarbonyl)-4-oxazolidinecarboxylic acid, (R)-(+)-3-(benzyloxycarbonyl)-4-oxazolidinecarboxylic acid, (4S)-3-(tert-butoxycarbonyl)-2,2-dimethyl-1,3-oxazolidine-4-carboxylic acid, 1-oxa-4-azaspiro[4.5]decane-3-carboxylic acid or the said compound wherein N is protected by Cbz, 1,8-dioxa-4-azaspiro[4.5]decane-3-carboxylic acid or the said compound wherein N is protected by Cbz.

Herein, references to "the compound" should be understood to be the thiazolidine carboxylic acid or oxazolidine carboxylic acid compound, unless otherwise specified.

In further preferred embodiments, the compound is selected from 2-(3-hydroxy-4-methoxy-phenyl)-thiazolidine-4-carboxylic acid, 2-(4-hydroxy-3-methoxyphenyl)-1,3-thiazolidine-4-carboxylic acid, 1,4-dioxa-9-thia-12-azadispiro [4.2.4.2] tetradecane-11-carboxylic acid, 2-(2-furyl)-1,3-thiazolidine-4-carboxylic acid, 2-(1-ethylpropyl)-4-thiazolidinecarboxylic acid, 1-thia-4-azaspiro[4.5]decane-3-carboxylic acid, 2-phenylthiazolidine-4-carboxylic acid, 2-[4-(allyloxy)phenyl]-1,3-thiazolidine-4-carboxylic acid, 2-hexyl-1,3-thiazolane-4-carboxylic acid, 2-(2-hydroxyphenyl)-thiazolidine-4-carboxylic acid, 2-benzyl-1,3-thiazolidine-4-carboxylic acid, 2,2-dimethyl-4-thiazolidine-4-carboxylic acid, 2-benzo(1,3)dixol-5-yl-thiazolidine-4-carboxylic acid, 2-(2-chloro-phenyl)-thiazolidine-4-carboxylic acid, 3-acetyl-2-phenyl-4-thiazolidinecarboxylic acid, 2-(5-bromo-2-hydroxyphenyl)thiazolidine-4-carobxylic acid, 1-oxa-4-azaspiro[4.5]decane-3-carboxylic acid wherein N is protected by CBz, 1,8-dioxa-4-azaspiro[4.5]decane-3-carboxylic acid wherein N is protected by CBz.

In further preferred embodiments, the compound is selected from 1-thia-4-azaspiro[4.5]decane-3-carboxylic acid, 2-hexyl-1,3-thiazolane-4-carboxylic acid or 2,2-dimethyl-4-thiazolidine-4-carboxylic acid.

In a deodorant composition, the compound typically presents at a concentration of at least 0.1 millimolar, preferably at least 0.5 millimolar, more preferably at least 1 millimolar, but up to 500 millimolar, preferably up to 100 millimolar, more preferably up to 50 millimolar. Accordingly, the compound is typically employed at a level of 0.001% by weight of the total composition, preferably at least 0.01 wt %, more preferably at least 0.1 wt %, even more preferably at least 0.2 wt %, but not more than 10%, preferably not more than 5%, more preferably not more than 2%, even more preferably not more than 1%. For example, the compound may be employed at a level of 0.5% by weight of the total composition. Herein, any of the upper limits can be combined with any of the lower limits.

The compound is preferably dispersed or solubilised in a deodorant composition. More preferably, the compound is solublilised.

The composition may comprise a delivery aid. By 'delivery aid' herein is meant a chemical that can increase or enhance the solubilisation of the compound in the deodorant composition. Preferably, the delivery aid is organic, for example an organic amino alcohol. The delivery aid may be an amino alkyl alcohol comprising at least 3 carbons, such as aminomethyl propanol. The weight ratio of the compound to the delivery aid is 1/20 to 20/1, preferably 1/10 to 10/1, more preferably 1/5 to 5/1.

A cosmetically acceptable carrier is an essential feature of the composition. The carrier is typically a fluid, in particular a liquid at 20° C. at atmospheric pressure. A carrier can be selected from water and/or organic carriers. Water is a preferred carrier, typically employed in a composition at a level of at least 20 wt %, more preferably at least 30 wt %, even more preferably at least 40 wt % and most preferably at least 60 wt % by weight of the total composition. The carrier may additionally or alternatively comprise an oil. Herein, the term 'oil' signifies a water-insoluble organic material that is liquid at 20° C. Any material having a solubility of less than 0.1 g/100 mL at 20° C. is considered to be insoluble. The oil can be selected from silicone oils, such as cyclic or linear silicones, examples including Dow Corning silicone fluids 344, 345, 244, 245, 246, 556, and the 200 series; Union Carbide Corporation Silicones 7207 and 7158; and General Electric silicone SF1202. Alternatively, or additionally, non-silicone oils may be used. Such materials include mineral oils, hydrogenated polyisobutene, polydecene, paraffins, isoparaffins of at least 10 carbon atoms, aliphatic or aromatic ester oils (e.g. isopropyl myristate, lauryl myristate, isopropyl palmitate, diisopropyl sebecate, diisopropyl adipate, or $C_8$ to $C_{18}$ alkyl benzoates), and polyglycol ethers, for example polyglycol butanol ethers. The total amount of carrier in the deodorant composition is typically from 10% to 99%, preferably from 25% to 99% by weight of the total composition. The ethanol level of the composition is preferably kept to a minimum, by which is meant the level is kept below 1%, preferably below 0.5% and more preferably below 0.1%. Most preferably, ethanol is completely absent from the composition.

A fragrance is also a preferred feature of the composition. The fragrance is typically composed of multiple different accords or notes and may be selected as desired. A fragrance is preferably used as a feature in methods of the invention. The presence of a fragrance may enhance the treating of body odour, whether by a masking effect or otherwise and may lead to a synergistic enhancement of the treatment. A fragrance may be in the form of a free (non-encapsulated) fragrance or it may be encapsulated in one of the multiple encapsulating materials used for this purpose. Encapsulated fragrance is a preferred feature of the composition, especially in the composition also comprising a free fragrance. A composition including both encapsulated and free fragrance can deliver enhanced, long-lasting treatment of body odour. Fragrance may be advantageously employed at a total level of from 0.1 to 6%, preferably 0.5 to 5% and more preferably at from 1 to 4% by weight of the total composition, excluding any volatile propellant that may be present therein.

Inorganic antimicrobial agents, in particular antiperspirant salts that are aluminium, zirconium and aluminium/ zirconium halides and halohydrate salts, are preferably absent from compositions of the invention. Hence, preferred compositions exclude any aluminium-containing antiperspirant active. In particularly preferred embodiments, both ethanol and inorganic antimicrobial agents, in particular antiperspirant salts that are aluminium, zirconium and aluminium/zirconium halides and halohydrate salts, are absent.

An organic antimicrobial agent may be an additional component of the composition, by which is meant an organic active that reduces microbial numbers when applied to the surface of the human body. This optional component can expand the range of microbes against which the composition is active. Organic antimicrobials are preferably used at a total level of from 0.1 to 1%.

Structurants and emulsifiers are further additional components of the compositions that are highly desirable in certain product forms. Structurants, when employed, are preferably present at from 1% to 30% by weight of the composition, whilst emulsifiers are preferably present at from 0.1% to 10% by weight of the composition. Suitable structurants include cellulosic thickeners such as hydroxy propyl cellulose and hydroxy ethyl cellulose, and dibenzylidene sorbitol. Other suitable structurants include sodium stearate, stearyl alcohol, cetyl alcohol, hydrogenated castor oil, synthetic waxes, paraffin waxes, hydroxystearic acid, dibutyl lauroyl glutamide, alkyl silicone waxes, and silica. Suitable emulsifiers include steareth-2, steareth-20, steareth-21, ceteareth-20, glyceryl stearate, cetyl alcohol, cetearyl alcohol, PEG-20 stearate, dimethicone copolyol, and poloxamines.

Further emulsifiers/surfactants desirable in certain compositions of the invention are perfume solubilisers and wash-off agents. Examples of the former include PEG-hydrogenated castor oil, available from BASF in the Cremaphor RH and CO ranges, preferably present at up to 1.5% by weight, more preferably 0.3 to 0.7% by weight. Examples of the latter include poly(oxyethylene) ethers. Certain sensory modifiers are further desirable components in the compositions. Such materials are preferably used at a level of up to 20% by weight of the composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, polysaccharides, corn starch, C12-C15 alcohol benzoate, PPG-3 myristyl ether, octyl dodecanol, C7-C14 isoparaffins, diisopropyl adipate, isosorbide laurate, PPG-14 butyl ether, glycerol, hydrogenated polyisobutene, polydecene, titanium dioxide, phenyl trimethicone, dioctyl adipate, and hexamethyl disiloxane.

The compounds identified by present invention represent a new class of deodorant actives that can be screened by the method disclosed herein. The method uses an odour-generating C-S β-lyase, in particular S. hominis B10 C-S β-lyase. In accordance with the procedure detailed in Example 1, the medium of the screening method comprises a 20 millimolar concentration of the compound to be screened. The medium further comprises S. hominis C-S β-lyase enzyme and 2 millimolar Cys-3M3SH. Following an incubation at 35° C. for a period of 24 hours, the reduction in 3M3SH released by S. hominis C-S β-lyase from Cys-3M3SH is measured. Herein, the inhibition of 3M3SH level is relative to a control without any compound being screened. In preferred embodiments, following the procedure detailed in Example 1, the medium comprises a 10 millimolar concentration of compound to be screened. In further preferred embodiments, the concentration of the compound to be screened can be 5 millimolar, preferably 2 millimolar, more preferably 1 millimolar, most preferably 0.5 millimolar.

Typically, the reduction of 3M3SH is considered 'significant' when it is at least 10%. Preferably, the reduction of 3M3SH is at least 20%, more preferably at least 40%, most preferably at last 80%.

The new class of deodorant compounds identified is an essential feature in the method of screening, the deodorant composition, the manufacturing process of said composition and the method of treating body odour as well as the method of inhibiting the identified C-S β lyase enzyme.

As has been mentioned above, present inventors surprisingly found a C-S β lyase which only exists in three of the Staphylococcus species. The enzyme was subsequently cloned from S. hominis strain B10. The classic inhibitors identified from prior art are only weakly active against this S. hominis C-S β lyase. However, the inventors have found the biotransformation of Cys-3M3SH to the thioalcohol 3M3SH by the enzyme can be suppressed by inhibiting the enzyme with a new class of active which is a thiazolidine- or, oxazolidine-carboxylic acid compound. As a result, biotransformation of precursor is reduced, thus reducing the generation of highly odorous 3M3SH.

The compound is used as a deodorant active in the deodorant composition. The cosmetic method of treating body odour comprises topical application of the composition, preferably sprayed onto the surface of human body. However, the composition may be applied by any suitable means. For example, application of a liquid composition may be by adsorption onto a carrier matrix like paper, fabric, or sponge and application by contacting said carrier matrix with the surface of human body. Solid or semi-solid compositions may be applied by direct contact or may be dissolved or dispensed in a liquid medium prior to application. Application may also comprise a combination of any two or more of the above techniques.

The invention may be illustrated by the following non-limiting examples.

EXAMPLE 1

The deodorant actives affecting S. hominis C-S β lyase are identified by using the following procedure. The Cys-3M3SH used in the procedure may be obtained using a method described in Chem. Biodivers., 2, 2005, 705-716. The purified S. hominis B10 C-S β lyase was prepared by cloning the gene encoding this enzyme into Escherichia coli using methodology known in the art. Recombinant S. hominis B10 C-S β-lyase was then expressed in E. coli and purified by immobilised metal ion affinity chromatography. M9 salts are mixtures of 6 g/L $Na_2HPO_4$, 3 g/L $KH_2PO_4$, 0.5 g/L NaCl, adjusted to pH 7.0 with NaOH.

Glass reaction tubes were set up, each containing 2 mM Cys-3M3SH (dissolved in M9 salts), 50 μM pyridoxal phosphate, purified S. hominis B10 C-S β lyase to a final concentration of 10 μg/ml, and M9 salts (or, where appropriate, a test material dissolved in M9 salts at, for example, 20 mM) to adjust the volume to 500 μl. Enzyme only (C-S beta-lyase) and substrate only (Cys-3M3SH) reactions were also included in each experiment. The reactions were incubated with shaking at 35° C. for 24 hours. To measure released 3M3SH, each reaction vial was first centrifuged at 13,000 rpm for 2 minutes. A volume of 0.095 ml labelling solution, consisting of 0.080 ml $dH_2O$, 0.010 ml Tris (pH 8.0) and 0.005 ml 5,5'-dithiobis-(2-nitrobenzoic acid) (DTNB) stock solution (50 mM sodium acetate, 2 mM DTNB, dissolved in dH₂O) was added to each well of a micro-titre plate. 0.005 ml of each reaction supernatant was added to the wells of the micro-titre plate, which was then incubated at room temperature for 5 minutes. Absorbance ($A_{412}$) values, which correlate with the concentration of 3M3SH present, were recorded using a spectrophotometer.

In most cases, the spectrophotometric method was inappropriate because the test materials possessed a chromophore or formed one during the course of the reaction. In these cases, a HPLC analysis was carried out according to the methodology described in J. Pharm. Biomed. Anal. 2008; 48:1375-80 and FEMS Microbiol. Lett., 263(16), 2015, fnv111.

TABLE 1

Effect of tested materials on the transformation of Cys-3M3SH to 3M3SH by purified *S. hominis* B10 C-S β lyase (material concentration = 20 millimolar)

| Ref | Test materials | % Inhibition |
|---|---|---|
| C1 | O-benzyl-D-serine | 8.2% |
| EX1 | 2-(3-hydroxy-4-methoxy-phenyl)-thiazolidine-4-carboxylic acid | 100% |
| EX2 | 2-(4-hydroxy-3-methoxyphenyl)-1,3-thiazolidine-4-carboxylic acid | 100% |
| EX3 | 1,4-dioxa-9-thia-12-azadispirol[4.2.4.2]tetradecane-11-carboxylic acid | 80.6% |
| EX4 | 2-(2-furyl)1,3-thiazolide-4-carboxylic acid | 80.4% |
| EX5 | 2-(1-ethylpropyl)-4-thiazolidine-4-carboxylic acid | 94.1% |
| EX6 | 1-thia-4-azaspiro[4.5]decane-3-carboxylic acid | 100% |
| EX7 | 8-benzyl-1-thia-4,8-diazaspiro[4.5]decane-3-carboxylic acid | 87.8% |
| EX8 | 2-phenylthiazolidine-4-carboxylic acid | 95.9% |
| EX9 | 2-(4-(allyloxy)phenyl)-1,3-thiazolidine-4-carboxylic acid | 100% |
| EX10 | 2-(4-methoxyphenyl)-1,3-thiazolidine-4-carboxylic acid | 88.2% |
| EX11 | 2-hexyl-1,3-thiazolane-4-carboxylic acid | 100% |
| EX12 | 2-(2-hydroxy-pheny)-thiazolidine-4-carboxylic acid | 100% |
| EX13 | (S)-(−)-3-(benzyloxycarbonyl)-4-oxazolidinecarboxylic acid | 41.2% |
| EX14 | (R)-(+)-3-(Benzyloxycarbonyl)-4-oxazolidinecarboxylic acid | 53.2% |
| EX15 | (4S)-3-(tert-Butoxycarbonyl)-2,2-dimethyl-1,3-oxazolidine-4-carboxylic acid | 45.2% |
| EX16 | 1-oxa-4-azaspiro[4.5]decane-3-carboxylic acid(N-CBz protected) | 93.0% |
| EX17 | 1,8-Dioxa-4-azaspiro[4.5]decane-3-carboxylic acid(N-CBz protected) | 84.2% |

EX1-17 are according to the invention whilst C1 is a known inhibitor of C-S β lyase from the prior art, not according to the invention. Data suggest EX1-17 are capable of supressing malodour by interaction with *S. hominis* C-S β lyase. The effect is significantly greater than the comparative example C1.

TABLE 2

Effect of tested materials on the transformation of Cys-3M3SH to 3M3SH by purified *S. hominis* B10 C-S β lyase (material concentration = 2 millimolar)

| Ref | Test materials | % inhibition |
|---|---|---|
| C1 | O-benzyl-D-serine | 0% |
| EX1 | 2-(3-hydroxy-4-methoxy-phenyl)-thiazolidine-4-carboxylic acid | 34.9% |
| EX2 | 2-(4-hydroxy-3-methoxyphenyl)-1,3-thiazolidine-4-carboxylic acid | 32.9% |
| EX3 | 1,4-dioxa-9-thia-12-azadispirol[4.2.4.2]tetradecane-11-carboxylic acid | 32.3% |
| EX4 | 2-(2-furyl)1,3-thiazolide-4-carboxylic acid | 20.8% |
| EX5 | 2-(1-ethylpropyl)-4-thiazolidenecarboxylic acid | 46% |
| EX6 | 1-thia-4-azaspiro[4.5]decane-3-carboxylic acid | 90.9% |
| EX7 | 8-benzyl-1-thia-4,8-diazaspiro[4.5]decane-3-carboxylic acid | 11.9% |
| EX8 | 2-phenylthiazolidine-4-carboxylic acid | 12.3% |
| EX9 | 2-(4-(allyloxy)phenyl)-1,3-thiazolidine-4-carboxylic acid | 39.7% |
| EX10 | 2-(4-methoxyphenyl)-1,3-thiazolidine-4-carboxylic acid | 24.5% |
| EX11 | 2-hexyl-1,3-thiazolane-4-carboxylic acid | 87.5% |
| EX12 | 2-(2-hydroxy-pheny)-thiazolidine-4-carboxylic acid | 46.5% |
| EX13 | 2,2-dimethyl-4-thiazolidine-4-carboxylic acid | 86.3% |
| EX14 | 2-(2-chloro-phenyl)-thiazolidine-4-carboxylic acid | 43.0% |
| EX15 | 2-benzo(1,3)dioxol-5-yl-thiazolidine-4-carboxylic acid | 38.8% |
| EX16 | 2-ethyl-thiazolidine-4-carboxylic acid | 29.6% |
| EX17 | 2-benzyl-1,3-thiazolidine-4-carboxylic acid | 67.6% |
| EX18 | (4S)-3-(tert-Butoxycarbonyl)-2,2-dimethyl-1,3-oxazolidine-4-carboxylic acid | 31.4% |
| EX19 | 1-oxa-4-azaspiro[4.5]decane-3-carboxylic acid(N-CBz protected) | 30.3% |
| EX20 | 1,8-Dioxa-4-azaspiro[4.5]decane-3-carboxylic acid(N-CBz protected) | 54.1% |

Data in Table 2 suggest the materials according to present invention are capable of suppressing malodour (3M3SH) at even 2 millimolar. In comparison, C1 not according to the present invention does not present significant reduction of malodour.

Example of Deodorant Compositions

TABLE 3

Roll-on deodorant composition

| INCI Name | % w/w | Trade Name |
|---|---|---|
| Alcohol denat | 63.00 | Absolute Ethanol |
| Hydroxypropylcellulose | 0.67 | Klucel MCS |
| Aminomethyl propanol | 0.1125 | AMP Ultra P02000 |
| (4R)-2-Hexylthiazolidine-4-carboxylic acid | 0.5 | (4R)-2-hexylthiazolidine-4-carboxylic acid |
| Aqua | 35.7175 | Demin water |

Water and ethanol was first mixed in an appropriated sized beaker. The thiazolidine-carboxylic acid compound ((4R)-2-hexylthiazolidine-4-carboxylic acid) according to the present invention was weighed and mixed with the ethanol and water. Aminomethyl propanol was weighed and added to the beaker, followed by Hydroxypropylcellulose. The content of the beaker was mixed after each addition with either mechanical shearing, or shearing by a spatula. After the addition of hydroxypropylcellulose, the content was preferably further sheared by a Silverson mixer for 5 minutes at 10000 rpm to ensure a homogenous product was obtained.

The invention claimed is:

1. A human deodorant composition comprising:
   (1) an oxazolidine-carboxylic acid compound; and
   (2) a cosmetic carrier;
   wherein the oxazolidine-carboxylic acid compound is:
      (i) a compound of formula (I);
      (ii) an ester of a compound of formula (I);
      (iii) a salt of a compound of formula (I); or
      (iv) a compound that releases a compound of formula (I) in use;

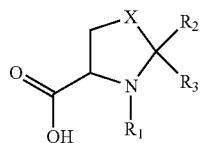

(I)

wherein X is O;
wherein $R_1$, $R_2$ and $R_3$ are same or different group;
wherein $R_1$ is hydrogen, C3-C20 linear alkyl, C3-C20 branched alkyl, C3-C20 cyclic alkyl, C3-C20 alkenyl, C3-C20 aryl residue, or mixtures thereof;
wherein $R_2$ and $R_3$ are each independently C3-C20 linear alkyl, C3-C20 branched alkyl, C3-C20 cyclic alkyl, C3-C20 alkenyl, C3-C20 aryl residue, mixtures thereof, or linked to form a cyclic structure;
wherein the deodorant composition is a topical deodorant composition; and wherein the cosmetic carrier comprise a water-insoluble organic material.

2. The deodorant composition according to claim 1, wherein $R_1$ is H.

3. The deodorant composition according to claim 1, wherein the oxazolidine-carboxylic acid compound is selected from the group consisting of (S) (−)-3-(benzyloxycarbonyl)-4-oxazolidinecarboxylic acid, (R)-(+)-3-(benzyloxycarbonyl)-4-oxazolidinecarboxylic acid, (4S)-3-(tert-butoxycarbonyl)-2,2-dimethyl-1,3-oxazolidine-4-carboxylic acid, 1-oxa-4-azaspiro[4.5]decane-3-carboxylic acid, 1-oxa-4-azaspiro[4.5]decane-3-carboxylic acid wherein N is protected by carboxybenzyl (Cbz), 1,8-dioxa-4-azaspiro[4.5]decane-3-carboxylic acid, and 1,8-dioxa-4-azaspiro[4.5]decane-3-carboxylic acid wherein N is protected by Cbz.

4. The deodorant composition according to claim 1, wherein the oxazolidine-carboxylic acid compound is present in an amount of 0.001% to 10% by weight based on a total weight of the deodorant composition.

5. The deodorant composition according to claim 1, further comprising a delivery aid for the oxazolidine-carboxylic acid compound, wherein the delivery aid is an amino alcohol comprising at least 3 carbons.

6. The deodorant composition according to claim 1, further comprising a fragrance.

7. A cosmetic method of treating malodour comprising topical application of a deodorant composition to a surface of human body, wherein the deodorant composition comprises:
   (1) an oxazolidine-carboxylic acid compound; and
   (2) a cosmetic carrier;
   wherein the oxazolidine-carboxylic acid compound is:
      (i) a compound of formula (I);
      (ii) an ester of a compound of formula (I);
      (iii) a salt of a compound of formula (I); or
      (iv) a compound that releases a compound of formula (I) in use;

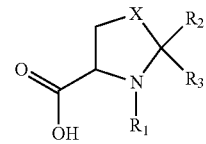

(I)

wherein X is O;
wherein $R_1$, $R_2$ and $R_3$ are same or different group;
wherein $R_1$ is hydrogen, C3-C20 linear alkyl, C3-C20 branched alkyl, C3-C20 cyclic alkyl, alkenyl, aryl residue, or mixtures thereof;
wherein $R_2$ and $R_3$ are each independently C3-C20 linear alkyl, C3-C20 branched alkyl, C3-C20 cyclic alkyl, alkenyl, aryl residue, mixtures thereof, or linked to form a cyclic structure.

8. The cosmetic method according to claim 7, wherein the oxazolidine-carboxylic acid compound inhibits C-S β layse.

9. The cosmetic method according to claim 7, further comprising: dissolving or homogenously dispersing the oxazolidine-carboxylic acid compound in the cosmetic carrier.

* * * * *